United States Patent [19]
Van Geloven

[11] Patent Number: 5,820,745
[45] Date of Patent: Oct. 13, 1998

[54] METHOD OF MEASURING THE CONCENTRATION OF A GAS IN A GAS MIXTURE AND ELECTROCHEMICAL SENSOR FOR DETERMINING THE GAS CONCENTRATION

[75] Inventor: Peter M. Van Geloven, Kessel-Lo, Belgium

[73] Assignee: Hergeus Electro-Nite International, N.V., Houthalen, Belgium

[21] Appl. No.: 849,573

[22] PCT Filed: Dec. 12, 1995

[86] PCT No.: PCT/EP95/04899

§ 371 Date: Jun. 16, 1997

§ 102(e) Date: Jun. 16, 1997

[87] PCT Pub. No.: WO96/18890

PCT Pub. Date: Jun. 20, 1996

[30] Foreign Application Priority Data

Dec. 16, 1994 [DE] Germany .......................... 44 45 033.8

[51] Int. Cl.⁶ .................................................. G01N 27/26
[52] U.S. Cl. ...................... 205/789; 205/780.5; 205/781; 205/783.5; 205/784; 205/786; 205/779.5; 205/782; 204/425; 204/426; 422/83; 422/88; 422/98
[58] Field of Search ................................ 205/789, 780.5, 205/781, 783.5, 784, 786, 779.5, 782; 204/425, 426; 422/83, 88, 98

[56] References Cited

U.S. PATENT DOCUMENTS

| | | | |
|---|---|---|---|
| 3,960,693 | 6/1976 | Weyl et al. | 204/195 S |
| 4,152,234 | 5/1979 | Pollner | 204/195 S |
| 4,190,499 | 2/1980 | Pebler | 204/1 T |
| 4,199,425 | 4/1980 | Sinkevitch | 204/195 S |
| 4,221,650 | 9/1980 | Friese et al. | 204/195 S |
| 4,547,281 | 10/1985 | Wang et al. | 204/424 |
| 5,344,549 | 9/1994 | Dees | 204/425 |
| 5,543,025 | 8/1996 | Garzon et al. | 204/425 |
| 5,736,028 | 4/1998 | Hjortsberg et al. | 204/425 |

FOREIGN PATENT DOCUMENTS

| | | |
|---|---|---|
| 0 019 731 A1 | 12/1980 | European Pat. Off. . |
| 0 310 063 A2 | 4/1989 | European Pat. Off. . |
| 0 294 085 B1 | 11/1992 | European Pat. Off. . |
| 2 470 383 | 5/1981 | France . |
| 32 38 824 A1 | 7/1983 | Germany . |
| 27 18 907 C2 | 4/1984 | Germany . |
| 32 39 850 A1 | 5/1984 | Germany . |
| 37 37 215 A1 | 5/1989 | Germany . |
| 43 43 748 A1 | 6/1994 | Germany . |

OTHER PUBLICATIONS

W. A. Fischer, D. Janke, *Mettallurgische Elecktrochemie*, Verlag Stahleisen m.b.H. Düsseldorf, Chapter 3.3.3.1, pp. 40–42, 1975. No month Available.

*Primary Examiner*—Bruce F. Bell
*Attorney, Agent, or Firm*—Panitch Schwarze Jacobs & Nadel, P.C.

[57] ABSTRACT

The invention relates to a method as well as to an electrochemical sensor for measuring the concentration of at least one predetermined gas in a gas mixture by means of an electrolyte provided with a first and a second surface-mounted electrode, which are exposed to the gas mixture together with the electrode connected to a voltage source, wherein the voltage source causes an electrical current flowing through the electrodes and electrolyte, which is dependent upon the ion concentration and is measured as an indicator of the gas concentration. In order to be able to dispense with reference measurements as well as diffusion holes or diffusion layers, gaseous molecules are adsorbed in the region of the first catalytically active electrode and the electrolyte, which are subsequently split into atoms and then either transformed into ions or subsequently participate in a chemical reaction, whereby the ion concentrations arising in both cases depend on the catalytic action of at lease one electrode and the gas concentration to be measured.

22 Claims, 6 Drawing Sheets

METHOD OF MEASURING THE CONCENTRATION OF A GAS IN A GAS MIXTURE AND ELECTROCHEMICAL SENSOR FOR DETERMINING THE GAS CONCENTRATION

This application is a 371 of PCT/EP95/04899 filed on Dec. 12, 1995.

BACKGROUND OF THE INVENTION

The invention relates to a procedure for measuring the concentration of at least one predetermined gas in a gas mixture by means of an electrolyte provided with a first and second surface-mounted electrode, which together with the electrode connected to a voltage source is exposed to the gas mixture, wherein the voltage source causes a flowing electrical current through electrodes and electrolyte which is dependent upon the ion concentration, and which is measured as an indicator of the gas concentration, as well an electrochemical sensor.

A procedure for determining fuels in a gas mixture with excess oxygen is known from U.S. Pat. No. 4,190,499, wherein the gas mixture is fed to the first and second electrodes on opposite sides of an oxygen ion-conducting solid state electrolyte, wherein the electrodes are provided with different materials having varying catalytic activity in relation to the gas mixture at a predetermined temperature. The difference which is generated in the oxygen potentials at the respective electrodes as a result of a varying catalytic activity forms an oxygen ion conductivity in the solid electrolyte cell which produces an electric signal in the strength which is characteristic for the combustion in the mixture at the moment, that is, for methane, oxygen, carbon and monoxide. The thermoelectric potential developed on the basis of the various electrode materials is evaluated either with regard to voltage or to current. In the event that no fuel or combustible material is present in the gas mixture, no potential difference is developed.

The procedure proves to be problematic on account of its comparatively expensive construction for generating the thermoelectric potential and, if need be, temperature regulation.

Furthermore, a polarographic measuring probe for determining the oxygen content in gases, especially in exhaust gases from internal combustion motors is known from EP-OS 0 019 731, which has an oxygen ion-conducting solid electrolyte element provided with an anode and a cathode on which a constant voltage is to be applied. The cathode is covered by a pore or channel-containing layer as a diffusion barrier and provided with catalytically active material with reference to the adjustment of the thermodynamic gas equilibrium, while the anode is made of a catalytically inactive material. Both electrodes are exposed to the gas to be measured in connection with the measuring probe operating according to the diffusion limiting current principle.

Here, limiting the current on the basis of the diffusion barrier and the thereby restricted measurement range proves to be especially problematic.

Furthermore, a process for determining the oxygen partial pressure and an oxygen partial pressure sensor is known from U.S. Pat. No. 5,344,549. A solid electrolyte with an alterable electron conductivity is provided with two electrodes, of which only one electrode, which is porously disconnected, is exposed to the gas to be measured, while the other electrode, as a so-called blocking electrode, is not exposed to the exhaust gas to be measured. A flow of oxygen within the solid electrolyte is not provided for.

A comparatively expensive construction of the sensor arises owing to the special sealing measures of the solid electrolyte.

A solid electrolyte exhaust gas sensor with two platinum electrodes is known from U.S. Pat. No. 4,199,425, which is provided for measuring oxygen and nitrogen oxides in exhaust gas. The outer platinum electrode is equipped with a rhodium-containing ceramic protective layer (aluminum oxide), whereby the addition of rhodium is supposed to make possible maintaining chemical equilibrium and nitrogen oxide measurement.

An electrochemical measuring probe for determining the oxygen content in gases, especially in exhaust gases of internal combustion engines, with a solid electrolyte and at least one electrode as a measuring probe is known from DE-OS 37 37 215, which is arranged on the side of the solid electrolyte exposed to the gas to be measured, wherein the measuring probe contains a porous ceramic protective layer of an aluminum oxide and/or a magnesium spinel matrix with zirconium dioxide particles embedded therein. Particles of platinum or a platinum alloy are added to the matrix of the protective layer as catalytically active material. Herein, one electrode is exposed to the gas mixture to be measured while the other is exposed to an additional reference gas.

An oxygen sensor for monitoring the oxygen content of exhaust gases from internal combustion motors is known from U.S. Pat. No. 4,221,650, which contains a solid electrolyte with oxygen-conducting zirconium dioxide, which is dispersed at 15 to 50% by volume in an aluminum oxide-containing oxide compound, wherein the solid electrolyte stands in contact with electrodes set at a distance to one another. The sensor is constructed as a cylindrical tube closed on one end, whereby zirconium dioxide is stabilized with yttrium oxide in the rounded-off, closed-off end. The electrodes are applied on both sides of the solid electrolytes, wherein the outer surface of the sensor is provided with a porous insulating layer, as for example magnesium spinel.

Furthermore, U.S. Pat. No. 3,960,693 describes an electrochemical device for measuring the oxygen concentration in exhaust gases, especially those from internal combustion engines, wherein a tube-shaped solid electrolyte with a passage which consists of two open ends set at a distance, wherein an internal circular shoulder is arranged between these two ends. A tube-shaped part made of an ion-conducting solid electrolyte possesses a closed-off first area which protrudes from one of the open ends and a second area which extends through the passage and is provided with an external circular flange. The tube-shaped part is provided with an electron-conducting catalytic layer, for example consisting of platinum, on its external surface as well as on its internal surface. The external applied layer, which is exposed to the ambient atmosphere, thereby serves as the measuring electrode.

An oxygen sensor with a tube-shaped solid electrolyte is known from U.S. Pat. No. 4,152,234. Its one end is closed. An internal electrode, on a platinum base and an external, catalytically active electron-conducting electrode, which likewise contains platinum and is applied to the outer surface of the sintered zirconium dioxide solid electrolyte by evaporation, cathodic evaporation, flame spraying or thick film technology, are situated in this end area.

An electrochemical element with a solid electrolyte is known from EP 0 294 085 B1, which consists of a dense, solid electrolyte body and a porous, solid electrolyte layer, wherein the cermet electrode applied in the exterior area of the closed end, preferably through mixing a powder from a platinum group metal, as for example, platinum, rhodium, palladium, iridium, ruthenium or osmium or a metal such as gold or nickel with a ceramic powder, such as zirconium oxide, hydrium oxide or aluminum oxide and, to be sure, such that the metallic powder amounts to no less than 40% of the volume. An electrode is likewise installed on the interior of the closed end as a reference electrode, which is exposed to the air as a reference gas. Consequently, it is possible to determine the oxygen partial pressure in the gas to be measured by means of electromotive force, which is generated between the first electrode and the second electrode.

The use of diffusion holes or diffusion layers, which can be polluted by exhaust gases upon use, proves to be problematic. In addition, reference measurements by means of a reference gas or reference electrode lead to comparatively expensive measurement arrangements or measurement processes.

SUMMARY OF THE INVENTION

The invention poses for itself the object of determining the concentration of at least one gas in a gas mixture by means of an electrochemical cell with electrodes charged with voltage, whereby reference measurements, for example, by means of a reference gas or reference electrode are to be dispensed with. Diffusion holes or diffusion layers, which can be polluted by exhaust gases from internal combustion motors, are also to be dispensed with. Furthermore, the determination of the concentration of various gases should be made possible by variation of the applied voltage and/or its polarity, and by the use of various electrode materials.

The object is accomplished with respect to a process for measuring the concentration wherein gaseous molecules are adsorbed, subsequently split up into atoms and then either transformed into ions or subsequently participate in a chemical reaction wherein the ion concentrations arising in both cases depend upon the catalytic action of at least one electrode and the gas concentration to be measured.

In this connection, it proves to be especially advantageous that the concentration of one gas through one measurement or the concentration of several gases through respectively several measurements can be conducted in a comparatively simple manner.

Advantageous embodiments of the process are given in dependent method claims.

The object is accomplished with respect to an electrochemical sensor for determining the concentration of a gas in a gas mixture wherein a first catalytically active electrode is provided for adsorption, ion transformation and/or chemical reaction, whereby the electrical current flowing through the electrolyte and electrodes is provided as a measured variable of the gas concentration.

In this connection, the comparatively simple manufacture and the possibility of measuring the concentrations of different gases in a simple manner proves to be advantageous.

Advantageous embodiements of the electrochemical sensor are given in dependent apparatus claims directed to the electrochemical sensor.

The comparatively simple manufacture of a planar type of sensors, which is based on the present invention, is to be regarded as especially advantageous. Such a planar configuration makes possible the production of an arrangement of several sensors in a single work step.

A further advantage is to be seen in the possibility of a temperature-dependent evaluation of the gas concentration with the aid of a temperature regulation of the sensor.

Furthermore, the use of rhenium is especially advantageous with respect to its specific catalytic activity in the detection of hydrocarbons.

BRIEF DESCRIPTION OF THE DRAWINGS

The subject is discussed hereafter in greater detail on the basis of FIGS. 1 to 7.

FIG. 4b shows a cross section along the line AB in FIG. 4a.

DETAILED DESCRIPTION OF THE INVENTION

Figure 1:
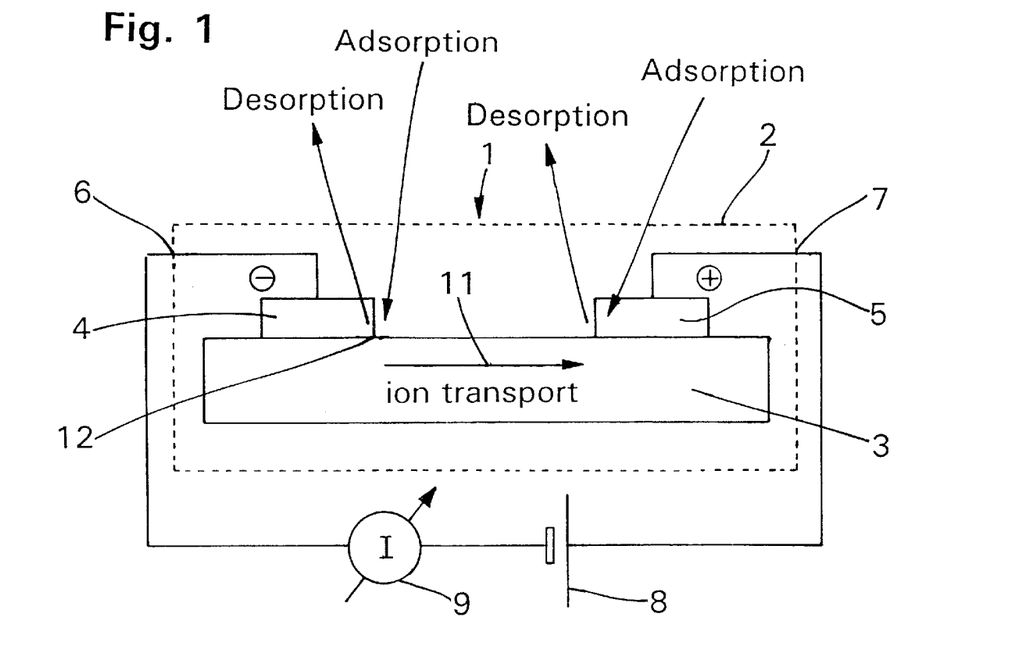
FIG. 1 shows the basic principle of the physical mode of operation of the present invention.

In accordance with FIG. 1, the sensor 2 of the invention is exposed to the gas phase 1. It has an electrolyte 3 which is preferably constructed as a solid electrolyte. The electrolyte 3, stands in electrical contact with a first electrode 4, as well as a second electrode 5, wherein the first electrode is constructed as a catalytically active element. The first electrode 4 is made of platinum or a platinum group metal, at least on its surface. The second electrode 5 is made of gold. The electrolyte 3 consists of zirconium dioxide stabilized with yttrium.

The electrodes 4, 5 of the sensor 2 are connected by a series connection of a voltage source 8 and an ammeter 9 over connections 6, 7.

Figure 2:
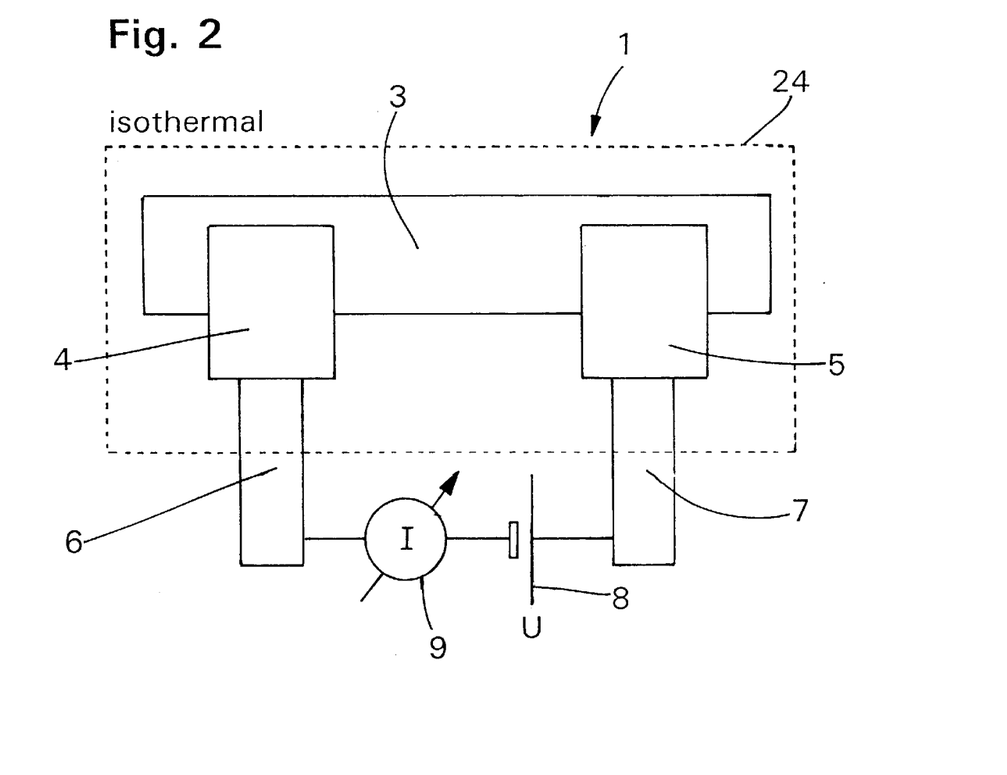
FIG. 2 shows a practical embodiment of the sensor with contacting of the electrolyte by applied electrodes.

A practical embodiment of the sensor is explained on the basis of FIG. 2. According to the embodiment there depicted, the electrolyte stands in contact with the electrodes 4, 5 which consist of various materials at least on their contacting surface. The first electrode preferably consists of platinum, the second of gold. The electrolyte corresponds to the electrolyte known from FIG. 1. The electrodes 4, 5 and the electrolyte 3 are thus arranged in an isothermal area 24, wherein the electrodes 4, 5 lead out of the thermally insulated area 24 over leads 6, 7 and are contacted outwardly. In this regard, it is very important that the leads 6, 7 do not come into contact with the electrolytes. Preferably the leads 6, 7 are made of the same material, for example platinum for both leads, so that a thermoelectric voltage owing to the isothermal area 24 can be avoided.

In accordance with FIGS. 1 and 2, the electrodes 4 and 5 as well as the solid electrolyte 3 are exposed to the gas 1 or gas phase to be analyzed in a typical manner. During the measurement process, one or more gas components are adsorbed and desorbed on the negative electrode 4. The first possibility consists in that a gas molecule is adsorbed on the electrode material. The adsorbed molecule is then subdivided into individual atoms, while it is adsorbed on the electrode material. The adsorbed molecule or the adsorbed atoms consequently wander to the contact area between the electrode 4, the gas phase 1 and the solid electrolyte 3. Such a contact area on which the three phases meet is designated as the triple point. It is provided with reference number 12 here. The line which is formed through triple points is called the triple line.

The second possibility consists in that gaseous components are directly adsorbed on the triple point. In each of these two cases, one of these adsorbed gaseous components can be the gas to be measured.

There exist two possibilities for the adsorbed molecules or adsorbed atoms at the triple points. A first possibility consists in them being transformed into anions, and to be sure through the incorporation of electrons which are present in the electrode material. In such a case, the electrolyte 3 should be a conductor for these anions and the gas to be measured should be composed of molecules which correspond with the anions. The material of the electrode 4 is chosen such that this reaction is promoted. This means that the material of the electrode 4 serves as a catalyst for the ionization reaction. A typical example can be seen in the oxygen molecules being transformed into oxygen atoms, and these oxygen atoms are transformed into $O_{2-}$ ions at the triple point 12 by taking up two electrons from electrode 4. Zirconium dioxide is to be viewed as a suitable electrolyte, as zirconium dioxide is a good conductor for $O_{2-}$ ions at high temperatures. Platinum has proved to be suitable material for the first electrode 4, while the second electrode 5 consists of gold.

The second possibility consists of a reaction occurring between two or more substances at the triple points. At least one of the substances should be present in adsorbed form and at least one of the substances should be the gas to be measured. In the event that an atom of type X is exchanged between the reacting substances with this reaction, then the electrolyte should be a conductor for ions of type X. An example for such a reaction is elaborated upon as follows:

$$2CO + 2NO \text{ - - - } 2CO_2 + N_2$$

In this case, two oxygen atoms are exchanged between nitrogen and carbon. Therefore, in such a case, the electrolyte should be an oxygen electron conductor, as is the case for zirconium dioxide. The type X ion is an oxygen ion in this case. As such, the concentration of these oxygen ions in the electrolyte in the vicinity of the triple point is important, as this influences the equilibrium between the reacting substances. The material of the electrode 4 is chosen in order to accelerate the reaction. This means that the material of the electrode 4 acts as a catalyst for the reaction. The number of anions which are conducted from electrode 4 to electrode 5 through electrolyte 3 depends upon the concentration of anions which are available on electrode 4. This concentration is determined by the chemical reaction in the vicinity of the triple point of electrode 4 and consequently by concentrating of gaseous substance which is supposed to be determined.

In general, the ion flow rate in the electrolyte is influenced by various factors. One of these factors is the extent of reaction catalysis through the material of electrode 4. Another factor is the concentration of the gas to be measured. Other factors include the voltage of the voltage source 8, the temperature, the size of the surface of electrodes 4 and 5. Since the ion flow rate through the electrolyte is directly proportional to the electric current which is measured by the ammeter 9, this current is also influenced by the concentration of the gas to be measured.

Assuming that the anions wander through the electrolyte from electrode 4 to electrode 5, these ions are recombined at electrode 5 whereby they are neutralized and recombine into gas molecules which are subsequently released into the gas atmosphere 1. This reaction is designated as the desorption reaction.

The step determining the rate of speed in the adsorption, reaction, wandering and desorption can also be associated with electrode 5, instead of with electrode 4, as was presented in the foregoing paragraphs. In this case, the electric current 1 is determined by the catalytic action of electrode 5. The electrode material of electrode 5 is very important in this case, more important than the material of electrode 4. The relative sizes of electrodes 4 and 5 also determine whether the step determining the rates of speed occurs on electrode 4 or electrode 5.

In this regard, it is not necessary that the materials of electrodes 4 and 5 have to be different. In the event that different types of materials are selected for the electrodes, it is possible to increase or reduce the sensitivity of the sensor by reversing the polarity of the electrodes. Presupposing that, for example, current I is measured by means of ammeter 9 using the electrical polarity in accordance with FIG. 1, this means that electrode 4 is connected with the negative pole and electrode 5 is connected with the positive pole of the electric voltage source 8. In the event that the ions of the electrolyte are negative ions, a current of ions will flow in accordance with ion transport arrow 11 in FIG. 1. Here it is assumed that the rate-determining step for the formation of ions and for the desorption reaction, as mentioned above, is bound to electrode 4. In this case, the catalytic activity of electrode 4 determines the strength of the electric current I. When the polarity of the electrical voltage is reversed, another current I will flow, as electrode 5 is made of another material than electrode 4. It is possible by selecting the materials of electrodes 4 and 5 to make the difference between the two measured currents as great as possible, whereby the sensitivity for the gas to be measured is increased. In most cases a high sensitivity is desired. In the event that the range of the gas concentration which is supposed to be measured is very high, it is desirable to have available various sensitivity ranges. This can likewise be realized with various electrode materials, whereby each results in a specific sensitivity to the gas to be measured.

Figure 3:
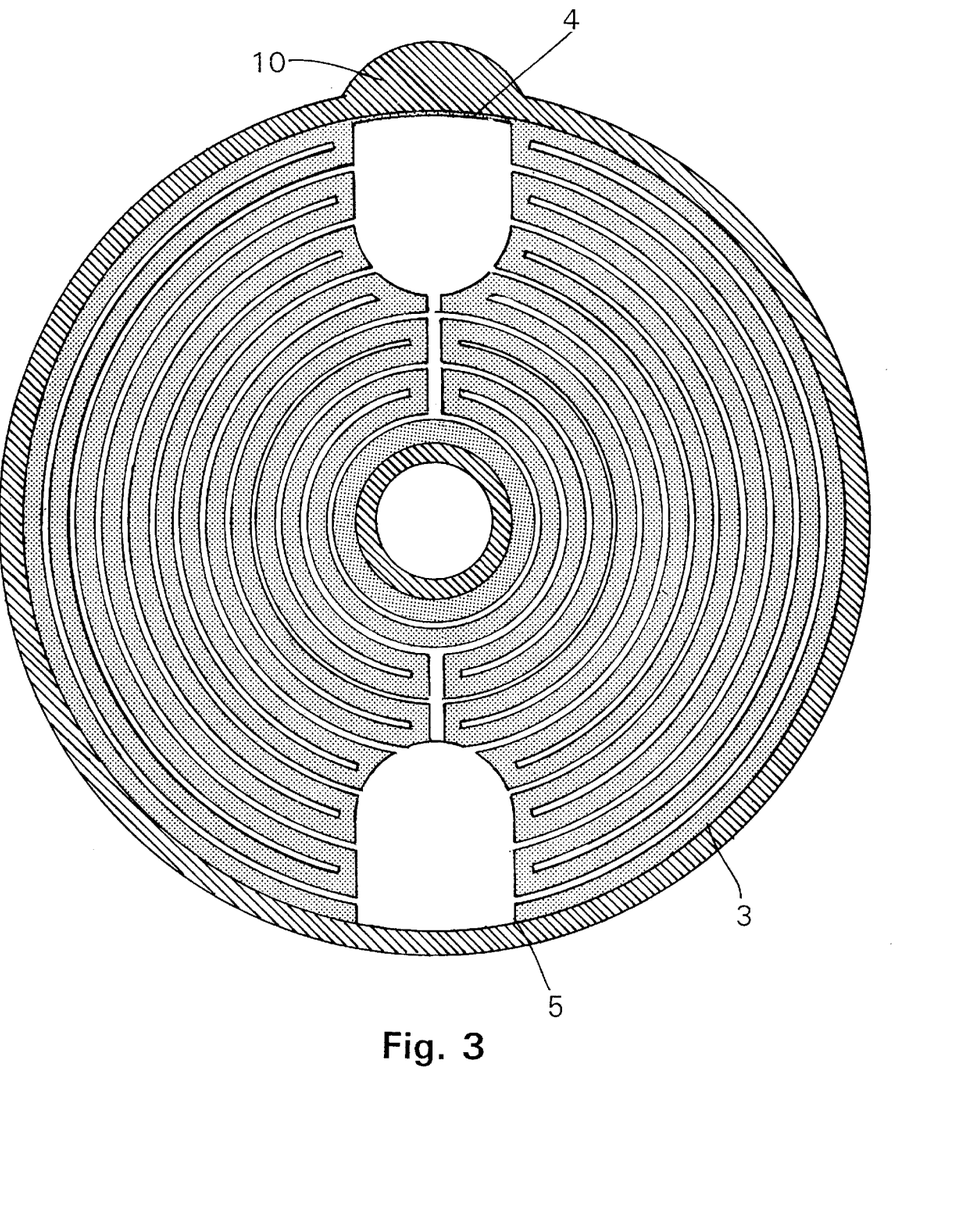
FIG. 3 shows a possible embodiment of the sensor in a planar mode of construction in accordance with the present invention.

A practical embodiment of a sensor of the present invention is presented in FIG. 3. FIG. 3 is an example of a planar oxygen sensor. A planar electrolyte 3 is applied to an inert substrate 10. The electrolyte consists of zirconium dioxide stabilized with yttrium oxide or magnesium oxide, the substrate of aluminum oxide. The electrolyte 3 is covered by planar electrodes 4, 5. Electrode 4 consists of platinum and electrode 5 of gold. In this case, the length of the triple line is as great as possible, in order to increase the flow of ions through the electrolyte, from which a high sensitivity results.

Figure 4A:
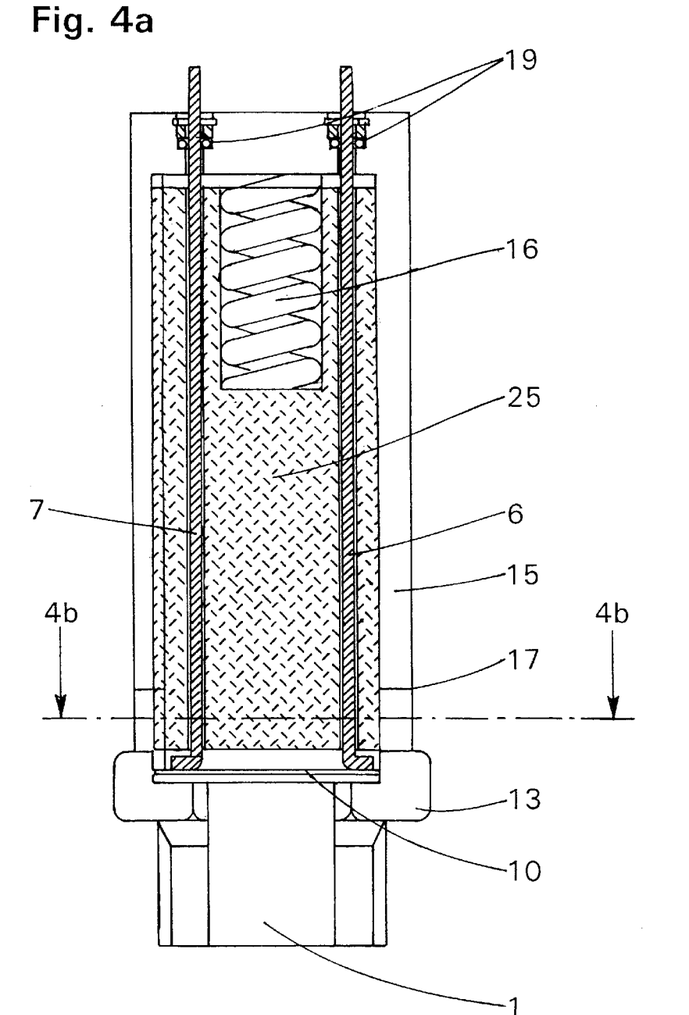
FIG. 4a shows a sensor housing for a sensor in accordance with FIG. 3 in longitudinal section.

FIG. 4a represents an exemplary practical embodiment for a sensor in accordance with FIG. 3, which is directed toward high temperature applications, for example in the exhaust gas systems of internal combustion motors. The substrate 10 of the sensor is arranged in the head area 13 of a metal housing 15. The head area 13 is screwed into an aperture provided with a thread. The head area 13 is made of a material capable of resisting heat. The connections 4, 5 of the electrodes are contacted by means of connection wires 6, 7 (see also FIGS. 3 and 2).

These connection wires 6, 7 are pressed upon the sensor substrate of the heat resistant and electrically insulating pressed body 25. The pressed body 25 consists of aluminum oxide. It can nonetheless also consist of cordierite or dichroite. Pressed body 25 is pressed upon the connection wires 6, 7 by means of the heat resistant spring 16. The metal housing 15 consists of heat resistant metal and is welded to the head area 13 in the edge area 17. The welding is conducted in a gas tight manner. In order to prevent gas leakage over connection wires 6, 7, a heat resistant 19 is used.

Figure 4B:
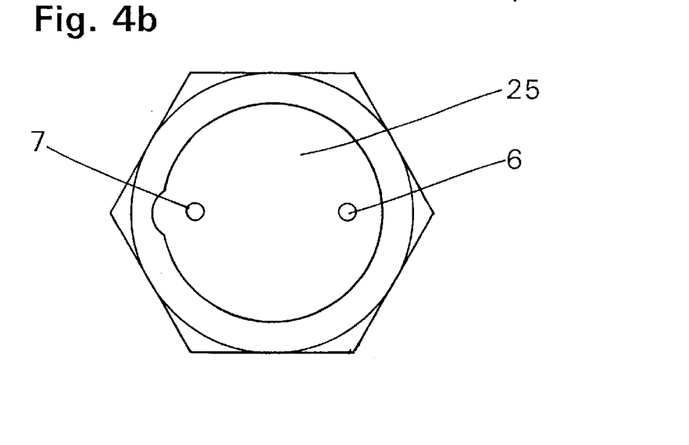

The pressed body 25 as well as the connection wires 6, 7 are recognizable in FIG. 4b in cross section taken along line AB of FIG. 4a.

Figure 5:
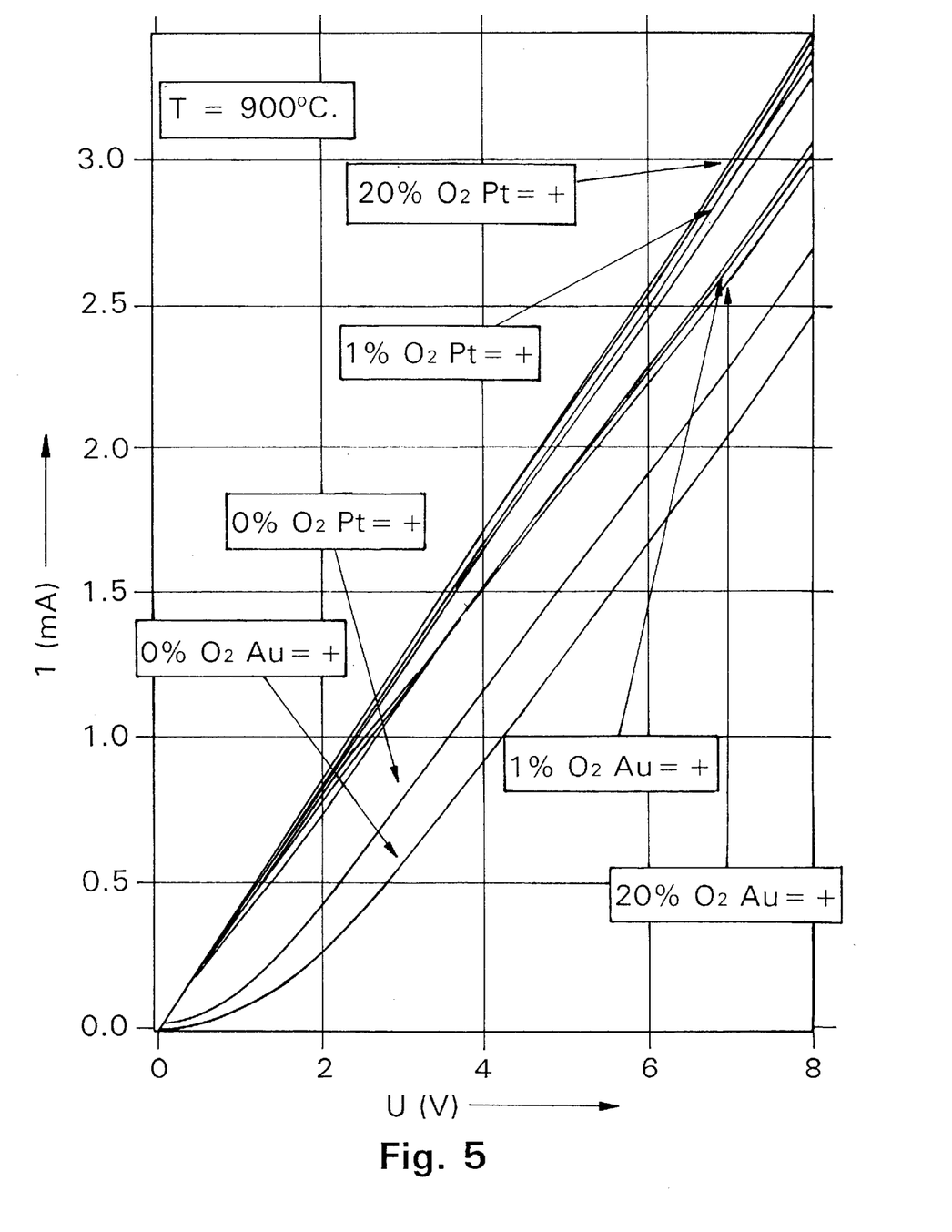
FIG. 5 shows characteristic curves of the current in a characteristic curve diagram as a function of the applied voltage for various oxygen concentrations at a temperature of 900° C., wherein zirconium dioxide stabilized with yttrium oxide is used as an electrolyte.

The characteristic curve diagram in accordance with FIG. 5 is directed toward an embodiment in which the sensitivity is increased by the use of two different electrode materials. The embodiment is directed toward a sensor with which zirconium dioxide stabilized with yttrium oxide is used as an electrolyte, the gas to be measured is oxygen, and the electrodes 4 and 5 consist respectively of platinum and gold. The temperature of the gas and the sensor amount to 900° C. Therein a difference is determined by means of reversing the polarity of the electrodes between the current, with which the platinum electrode is set as the positive pole and the current with which the gold electrode is set as the positive pole, from which a higher sensitivity with respect to the oxygen content results, than in the case where the polarity is not changed. This corresponds to the fact that in the event the gold electrode is set as the positive pole, the current I is diminished with rising oxygen concentration, while the current I is increased when the platinum electrode is set positive. Here it must be taken into consideration that such a sensor can also be used without changing the polarity of the voltage source.

According to FIG. 5, the curves A, B and C hold for a positively switched platinum electrode, wherein curve A holds for an oxygen content of 0%, curve B for an oxygen content of 1% and curve C for an oxygen content of 20%. In this connection, it can be recognized that with an applied voltage of 6 V in accordance with curve A, a current of ca. 1.90 mA is obtained, according to curve B, a current of ca. 2.44 mA, and according to curve C, a current of ca. 2.56 mA. If polarity is reversed, the gold electrode is set positive, whereby curve D applies for an oxygen content of 0%, curve E for an oxygen content of 1%, curve F for an oxygen content of 20%. This means that with an applied voltage of 6 V, a current of ca. 1.67 mA is received according to curve D, whereby the difference from curve A amounts to 0.23 mA. For curve E, a current of ca. 2.28 mA is obtained, so that the difference between corresponding curve B lies at 0.16 mA. In accordance with curve F, the amperage lies at 2.21 mA, from which a difference of 0.35 mA in comparison with curve C (20% oxygen component) results.

Figure 6:
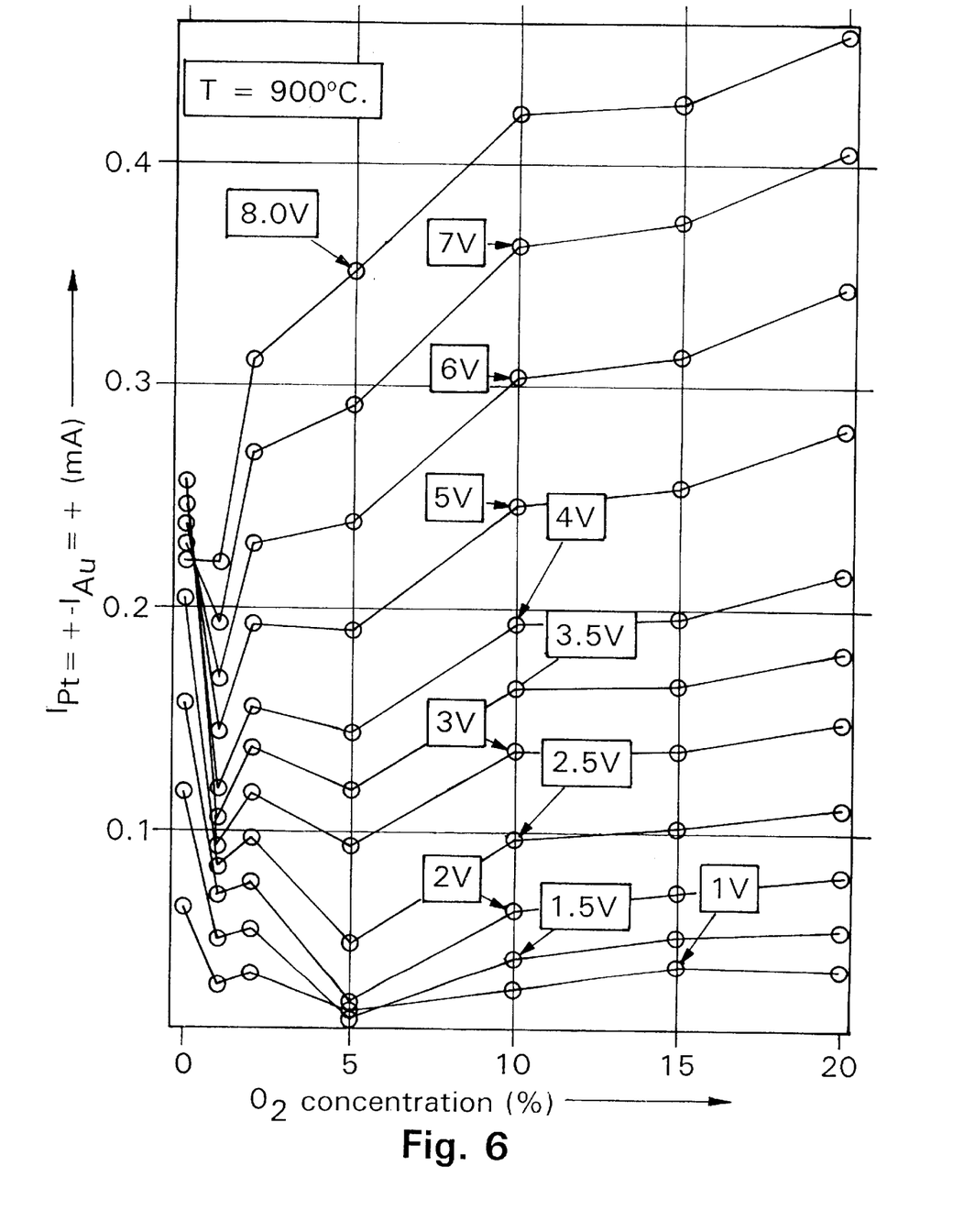
FIG. 6 shows characteristic curves in a characteristic curve diagram of a differential current as a function of the oxygen concentration for applied voltages of various heights in the case of a zirconium dioxide electrolyte stabilized with yttrium oxide, wherein the differential current is obtained through reversing polarity of an electrode pair of planar gold and platinum electrodes. The temperature amounts to 900° C.

FIG. 6 presents the difference between the two currents I for a positive platinum electrode and a positive gold electrode as a function of the oxygen concentration c, which can be directly derived from the experimental result of FIG. 5. As is recognizable from the group of curves in this figure, the sensitivity for oxygen also depends on the height of electrical voltage.

Figure 7:
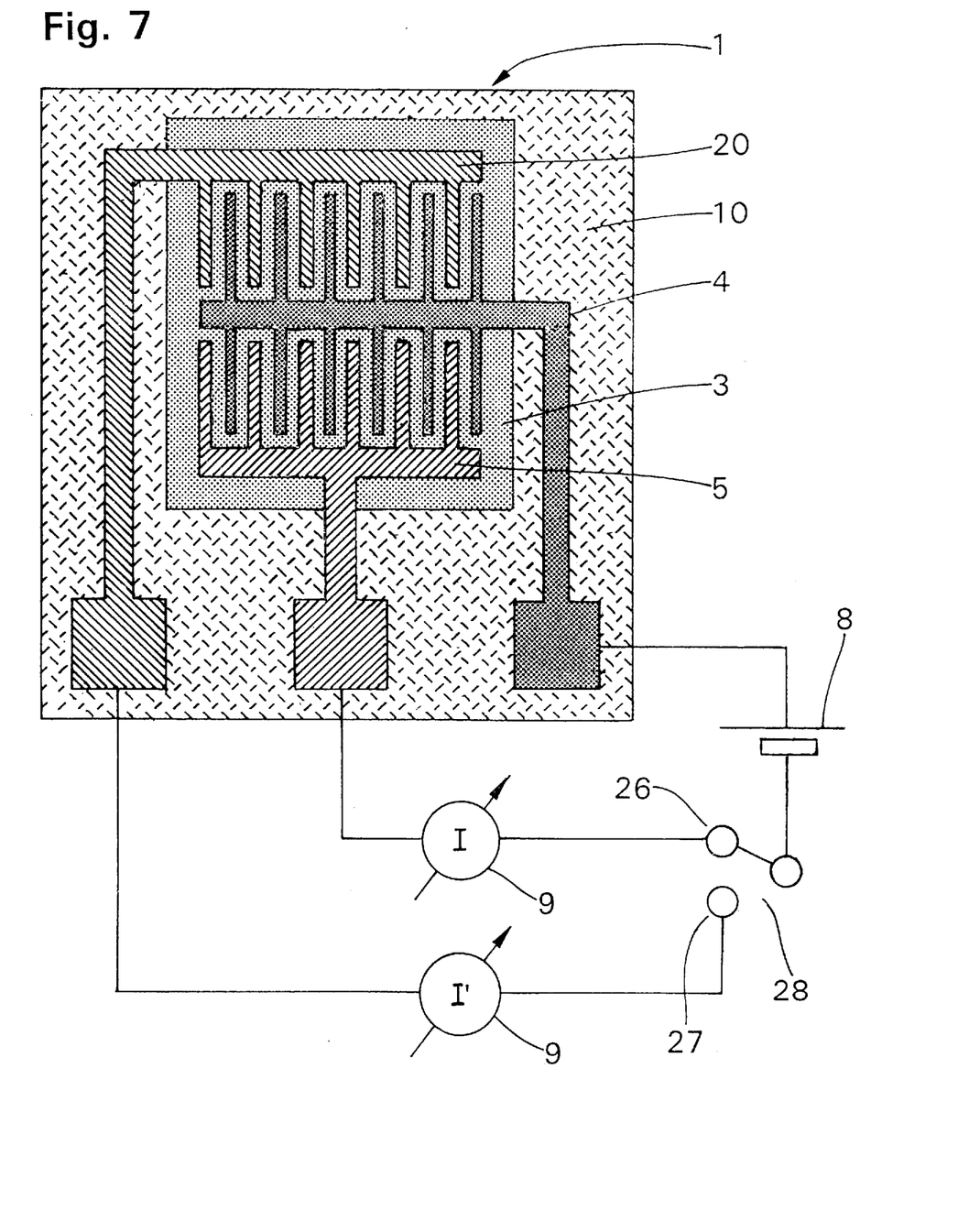
FIG. 7 shows the embodiment of a sensor with more than two electrodes, based on the present invention.

FIG. 7 represents an embodiment of a sensor with more than two electrodes, in which the procedure of the invention is used. As is evident from this figure, the sensor has a planar construction. The electrolyte 3 is covered by three electrodes 4, 5 and 20. The electrodes 4, 5, 20 are made of similar or different types of materials which, however, depends upon the gas to be investigated. When measuring oxygen content, for example, electrode 4 is made, for example, of platinum, electrode 5 of gold and electrode 20 of platinum. Zirconium dioxide stabilized by yttrium oxide or magnesium oxide is used as the electrolyte 3. The first current to be measured flows through electrodes 4 and 5. The second current I' to be measured flows through electrodes 4 and 20. For the case depicted in FIG. 7, polarity and the height of the electrical voltage are not changed. An alternative is to be seen in changing polarity and/or the amount of the voltage between position 26 and/or position 27 of the reversing switch 28. More than two current measurements result from this. Here it is important that the number of the gas concentrations to be determined cannot exceed the number of currents measured.

I claim:

1. Method for measuring the concentration of at least one predetermined gas in a gas mixture by means of an electrolyte provided with a first and a second surface-mounted electrode, which together with the electrode connected to a voltage source are exposed to the gas mixture, whereby the voltage source causes an electrical current flowing through the electrodes and electrolytes, which depends on the ion concentration and is measured as indicator of the gas concentration, characterized in that gaseous molecules are adsorbed in the area of the first catalytically active electrode and the electrolyte, subsequently split up into atoms and then either transformed into ions or subsequently participate in a chemical reaction, whereby the ion concentrations arising in both cases depends upon the catalytic action of at least one electrode and the gas concentration to be measured.

2. Method according to claim 1, characterized in that the catalytic activity of the first or second electrode determines the ion flow in the electrolyte and the electric current.

3. Method according to claim 1, characterized in that the voltage on the electrodes is switched between two or more different values, whereby each of the different voltage values has as a consequence another current as a measure for the gas concentration.

4. Method according to claim 1, characterized in that the polarity is switched on the electrodes, whereby each polarity has as a consequence a different current as a measure for the gas concentration.

5. Method according to claim 1, characterized in that the temperature of the sensor is regulated.

6. Electrochemical sensor for determination of the concentration of a gas in a gas mixture, especially the proportion of oxygen in exhaust gases of internal combustion motors, wherein an electrolyte together with two electrodes applied thereto is exposed to a gas mixture, and wherein an electrical voltage is applied to the electrodes, which causes a current which flows through the electrolyte, characterized in that a first catalytically active electrode (4, 5, 20) is provided for adsorption, ion transformation and/or chemical reaction, whereby the electrical current flowing through the electrolyte (3) and electrodes (4, 5, 20) is provided as a measured variable of the gas concentration.

7. Electrochemical sensor according to claim 6, characterized in that at least a second catalytically active electrode (4, 5, 20) is provided for adsorption, ion transformation and/or chemical reaction.

8. Sensor according to claim 6, characterized in that the first and at least second electrodes (4, 5, 20) have a varying catalytic activity.

9. Electrochemical sensor according to claim 6, characterized in that at least two electrodes (4, 5, 20) are made of different materials.

10. Electrochemical sensor according to claim 6, characterized in that more than two electrodes (4, 5, 20) are applied to the electrolyte (3), which is provided for determination of the concentration of several gases.

11. Electrochemical sensor according to claim 6, characterized in that the size and/or polarity of the voltage or voltages on the electrodes (4, 5, 20) can be altered.

12. Electrochemical sensor according to claim 6, characterized in that the electrodes (4, 5, 20) have a noble metal or noble metal alloy as a main component.

13. Electrochemical sensor according to claim 12, characterized in that at least one of the electrodes contains gold, platinum, rhodium or palladium.

14. Electrochemical sensor according to claim 12, characterized in that at least one of the electrodes (4, 5, 20) has a metal oxide.

15. Electrical sensor according to claim 12, characterized in that at least one of the electrodes contains silver.

16. Electrochemical sensor according to claims 6, characterized in that at least one of the electrodes (4, 5, 20) contains cerium oxide or rhodium for determination of nitrogen oxides.

17. Electrochemical sensor according to claim 6, characterized in that the electrolyte (3) is constructed as a solid electrolyte.

18. Electrochemical sensor according claim 17, characterized in that zirconium dioxide is used as the electrolyte (3).

19. Electrochemical sensor according to claim 18, characterized in that the zirconium dioxide is stabilized by yttrium oxide.

20. Electrochemical sensor according to claim 18, characterized in that the zirconium dioxide is stabilized by at least an oxide of yttrium, magnesium, calcium, cerium or samarium.

21. Electrochemical sensor according to claim 6, characterized in that at least one of the electrodes contains rhenium.

22. Electrochemical sensor according to claim 6, characterized in that at least the portion of the electrodes (4, 5, 20) exposed to the gas mixture is provided with a porous, non-catalytic protective coating.

* * * * *